US012642759B2

(12) United States Patent
Jung et al.

(10) Patent No.: US 12,642,759 B2
(45) Date of Patent: Jun. 2, 2026

(54) COSMETIC COMPOSITION FOR IMPROVING SKIN CONTAINING EXTRACTS OF POLYGALA TENUIFOLIA, ANGELICA DAHURICA AND ELSHOLTZIA SPLENDENS

(71) Applicant: SOOY-K CO., LTD., Seongnam-si (KR)

(72) Inventors: Youn Ok Jung, Hwaseong-si (KR); Ji Sun Chung, Seongnam-si (KR); Kyoung Mo Chung, Seoul (KR); Seo A Jung, Seongnam-si (KR); Ga Hyeon Song, Seongnam-si (KR)

(73) Assignee: SOOY-K CO., LTD., Seongnam-si (KR)

( * ) Notice: Subject to any disclaimer, the term of this patent is extended or adjusted under 35 U.S.C. 154(b) by 278 days.

(21) Appl. No.: 18/538,219

(22) PCT Filed: Dec. 4, 2023

(86) PCT No.: PCT/KR2023/019755
§ 371 (c)(1),
(2) Date: Dec. 13, 2023

(87) PCT Pub. No.: WO2025/105566
PCT Pub. Date: May 22, 2025

(65) Prior Publication Data
US 2025/0177284 A1　　Jun. 5, 2025

(30) Foreign Application Priority Data
Nov. 15, 2023　(KR) ........................ 10-2023-0157992

(51) Int. Cl.
*A61Q 19/00* (2006.01)
*A61K 8/9789* (2017.01)
(Continued)

(52) U.S. Cl.
CPC .......... *A61K 8/9789* (2017.08); *A61K 36/232* (2013.01); *A61K 36/53* (2013.01);
(Continued)

(58) Field of Classification Search
None
See application file for complete search history.

(56) References Cited

FOREIGN PATENT DOCUMENTS

| KR | 10-1287052 B1 | 7/2013 |
| KR | 10-2022-0148707 A | 11/2022 |
| KR | 10-2490447 B1 | 1/2023 |

OTHER PUBLICATIONS

Lee, Tae Bum et al., "Biological Activities of Cosmetic Material from Ten Kinds of Flower Ethanol Extracts", Korean Journal of Medicinal Crop Science, 28 (4), 2020, pp. 260-275.
(Continued)

*Primary Examiner* — Amjad Abraham
(74) *Attorney, Agent, or Firm* — Bridgeway IP Law Group, PLLC; Jihun Kim

(57) ABSTRACT
A composition for improving skin comprising extracts of *Polygala tenuifolia, Angelica dahurica* and *Elsholtzia splendens* is described. The composition is excellent in effects of improving skin inflammation, antioxidant effects, antibacterial effects on skin, and skin moisturizing effects, and thus can be used as a cosmetic for improving skin, and further, as a pharmaceutical composition for treating inflammatory skin diseases.

9 Claims, 6 Drawing Sheets

(51) Int. Cl.

| | |
|---|---|
| *A61K 36/232* | (2006.01) |
| *A61K 36/53* | (2006.01) |
| *A61K 36/69* | (2006.01) |
| *A61Q 17/00* | (2006.01) |

(52) U.S. Cl.
CPC ............ *A61K 36/69* (2013.01); *A61Q 17/005* (2013.01); *A61Q 19/00* (2013.01)

(56) References Cited

OTHER PUBLICATIONS

Jung, Seo A, et al., "Optimization of Mixing Ratio of Polygala Tenuifolia, Angelica Dahurica and Elsholtzia Splendens Extracts for Cosmetic Material Development", The Journal of the Convergence on Culture Technology, vol. 9, No. 6, Nov. 2023, pp. 993-1000, doi:10.17703/JCCT.2023.9.6.993.

Examiner, "Office Action for Korea Application No. 10-2023-0157992", Nov. 22, 2025, KIPO, Korea.

Oh, Hyun-Suk et al., "Anti-inflammatory activity of the water extract of Polygala tenuifolia Willd", Daehan one room Internal Medicine journal. Jun. 30, 2013, pp. 204-214, vol. 34, (2), Korea.

Lee, Tae Bum et al., "Biological Activities of Cosmetic Material from Ten Kinds of Flower Ethanol Extracts", Korean Journal of Medicinal Crop Science, Aug. 30, 2020, pp. 260-275, vol. 28, issue 4, Korea.

COSMETIC COMPOSITION FOR IMPROVING SKIN CONTAINING EXTRACTS OF POLYGALA TENUIFOLIA, ANGELICA DAHURICA AND ELSHOLTZIA SPLENDENS

TECHNICAL FIELD

This invention was carried out with the support of the Ministry of SMEs and Startups under the unique task number 1425174040 and task number S3289410. The research management professional institution for this project is the Small and Medium Enterprise Technology Information Promotion Agency. The research business name is "Announcement of the Implementation Plan for the Second Half of the 2022 Small Business Technology Innovation Development Project 'Market Responsive Type (General Project)'". The research subject name is "Development of Cosmetic Composition Including Fermented Extracts of *Agastache Rugosa, Dictamnus Albus*, and *Polygonatum Odoratum* for Improving Atopic Dermatitis and Itching Utilizing Anti-inflammatory and Skin Moisturizing Effects". The leading organization is SOOY-K Co., Ltd., and the research period is from Jul. 25, 2022, to Dec. 31, 2023.

The present invention relates to a cosmetic composition for improving skin comprising extracts of *Polygala tenuifolia, Angelica dahurica* and *Elsholtzia splendens*, more specifically, a cosmetic composition that has effects of improving skin inflammation, antioxidant effects, antibacterial effects on skin, and skin moisturizing effects.

BACKGROUND ART

Due to concerns about the side effects and chronic uses of chemical compounds, environmentally friendly natural substances derived from plants have recently been attracting attention as cosmetic materials, and researches on various bioactive ingredients of natural products are actively being conducted. Natural products contain various bioactive ingredients such as vitamins, minerals, polyphenols, etc., have excellent effects, and are guaranteed to be safe. Currently, there are various types of medicinal plants used for cosmetic purposes. Also, as interest in medicinal plants with efficacy and effects increases, researches on material development are actively underway. As a result, in response to the desire to improve health and maintain beautiful skin, natural products with effects such as relieving itching, promoting hair growth, improving wrinkles, whitening, moisturizing skin, removing dead skin cells, improving acne, blemishes, and skin, etc. are being applied to cosmetics.

However, plant extracts used in existing cosmetic compositions often have limitations due to their limited efficacy, stability issues, potential for skin irritation, etc. For example, some extracts may cause allergic reactions when applied directly to the skin, while others may have reduced efficacy when stored for long periods of time. In addition, cosmetic compositions based on natural products have a problem in ensuring consistent quality due to inconsistent manufacturing methods and the difficulty in standardizing raw materials. These problems suggest a need for new approaches for effective and safe use of natural product-based cosmetics.

Thus, there is an emerging need for new natural product raw materials that can improve the problems of existing natural product-based cosmetics and cosmetic compositions using the same.

SUMMARY OF INVENTION

Technical Problem

The present inventors prepared a composition containing extracts of *Polygala tenuifolia, Angelica dahurica* and *Elsholtzia splendens* as active ingredients, and found that the composition according to the present invention is excellent in effects of improving skin inflammation, antioxidant effects, antibacterial effects on skin, and skin moisturizing effects.

Thus, an object of the present invention is to provide a cosmetic composition for improving skin comprising extracts of *Polygala tenuifolia, Angelica dahurica* and *Elsholtzia splendens.*

Another object of the present invention is to provide a composition for treating inflammatory skin diseases comprising extracts of *Polygala tenuifolia, Angelica dahurica* and *Elsholtzia splendens.*

Yet another object of the present invention is to provide a food composition for improving inflammatory skin diseases comprising extracts of *Polygala tenuifolia, Angelica dahurica* and *Elsholtzia splendens.*

Solution to Problem

The present invention relates to a cosmetic composition for improving skin comprising extracts of *Polygala tenuifolia, Angelica dahurica* and *Elsholtzia splendens*. The composition according to the present invention is excellent in effects of improving skin inflammation, antioxidant effects, antibacterial effects on skin, and skin moisturizing effects.

Hereinafter, the present invention will be described in more detail.

An aspect of the present invention is a cosmetic composition for improving skin comprising a *Polygala tenuifolia* extract, an *Angelica dahurica* extract and an *Elsholtzia splendens* extract as active ingredients.

As used herein, the term "*Polygala tenuifolia*" refers to a perennial herb belonging to the family Polygalaceae. The core part of the root is removed and the rest is dried for use. It has been reported to have a potential to be developed for protection against nerve damage, and as antidepressants, painkillers, antifungals, anticancer agents, etc.

As used herein, the term "*Angelica dahurica*" refers to the dried root of *Angelica* belonging to the family Umbeliferae and which is effective in soothing, removal of fever, and relieving pain. It contains a large amount of sugars, minerals, essential oils, and more than 20 types of coumarin. The results of researches on *Angelica dahurica* reported that it has drug-metabolizing enzyme inhibitory and metabolism inhibitory activity and antithrombotic effects.

As used herein, the term "*Elsholtzia splendens*" refers to an annual herb belonging to the genus *Elsholtzia* of the family Labiatae. It is a Korean aromatic edible plant that emits a unique scent from the whole plant. It was known to be effective for coughing, sweating, pain, inflammation, fever, etc. and has been used as an ingredient in folk remedies.

As used herein, the term "cosmetic composition" may refer to, but not limited to, a formulation selected from the group consisting of solutions, ointments for external use, creams, foams, nourishing tonics, softening tonics, perfumes, packs, softening water, emulsions, makeup bases, essences, soaps, liquid cleansers, bath preparations, sunscreen creams, sun oils, suspensions, emulsions, pastes, gels, lotions, powders, soaps, surfactant-containing cleansers, oils, powder foundations, emulsion foundations, wax foundations, patches and sprays.

As used herein, the term "improving skin" may refer to one or more selected from the group consisting of skin moisturizing, skin soothing, skin regeneration, improvement of skin inflammation, wrinkle improvement, elasticity improvement, skin whitening, antioxidation, anti-aging, skin protection from external irritation, soothing sensitive skin, improvement of sensitive skin, alleviating erythema, alleviating itching, strengthening skin barrier function, alleviating skin irritation, antibacterial effects on skin, and alleviating skin pain.

As used herein, the term "skin inflammation" refers to diseases that include various inflammatory reactions which occur in the skin. These diseases show symptoms such as skin redness, itchiness, rash, and swelling, and are sometimes accompanied by pain. The causes of skin inflammation are diverse, including allergic reactions, infections, autoimmune reactions, and environmental factors. It may also be caused by an individual's lifestyle or genetic factors. In the present invention, the skin inflammation may be, but not limited to, dermatitis, allergic dermatitis, irritant dermatitis, seborrheic dermatitis, atopic dermatitis, sensitive skin diseases, pruritus, eczematous skin diseases, dry eczema, erythema, urticaria, psoriasis, drug rash, and acne.

In the present invention, the *Polygala tenuifolia* extract may be extracted from one or more selected from the group consisting of leaves, roots, stems, and fruits, but is not limited thereto.

In the present invention, the *Angelica dahurica* extract may be extracted from one or more selected from the group consisting of leaves, roots, stems, and fruits, but is not limited thereto.

In the present invention, the *Elsholtzia splendens* extract may be extracted from one or more selected from the group consisting of leaves, roots, stems, and fruits, but is not limited thereto.

In the present invention, the *Polygala tenuifolia* extract according to the present invention may include a solvent crude extract, a specific solvent-soluble extract (solvent fraction), and a solvent fraction of a solvent crude extract. It may be a crude extract obtained by extracting one or more selected from the group consisting of the leaves, roots, stems, and fruits of *Polygala tenuifolia* with one or more solvents selected from the group consisting of water and straight-chain or branched alcohols having 1 to 4 carbon atoms.

In the present invention, the *Angelica dahurica* extract according to the present invention may include a solvent crude extract, a specific solvent-soluble extract (solvent fraction), and a solvent fraction of a solvent crude extract. It may be a crude extract obtained by extracting one or more selected from the group consisting of the leaves, roots, stems, and fruits of *Angelica dahurica* with one or more solvents selected from the group consisting of water and straight-chain or branched alcohols having 1 to 4 carbon atoms.

In the present invention, the *Elsholtzia splendens* extract according to the present invention may include a solvent crude extract, a specific solvent-soluble extract (solvent fraction), and a solvent fraction of a solvent crude extract. It may be a crude extract obtained by extracting one or more selected from the group consisting of the leaves, roots, stems, and fruits of *Elsholtzia splendens* with one or more solvents selected from the group consisting of water and straight-chain or branched alcohols having 1 to 4 carbon atoms.

In the present invention, when a mixture of water and alcohol is used to prepare a crude extract, it may be an aqueous solution of 70% or more to less than 100% straight-chain or branched alcohol with 1 to 4 carbon atoms.

Additionally, the aqueous alcohol solution may be one or more selected from the group consisting of an aqueous methanol solution, an aqueous ethanol solution, an aqueous propanol solution, and an aqueous butanol solution.

The extract of *Polygala tenuifolia, Angelica dahurica* or *Elsholtzia splendens* according to the present invention may be a solvent fraction obtained by fractionating a solvent crude extract with an additional solvent, for example, a solvent fraction obtained from a solvent crude extract using one or more solvent selected from the group consisting of chloroform, ethyl acetate, and hexane.

In the present invention, the cosmetic composition may be a mixture of the *Polygala tenuifolia* extract, the *Angelica dahurica* extract and the *Elsholtzia splendens* extract in a specific ratio.

In an embodiment of the present invention, the *Polygala tenuifolia* extract, the *Angelica dahurica* extract and the *Elsholtzia splendens* extract may be mixed at a weight ratio of 0.05-3:0.05-3:0.05-3 (w/w), and for example, the *Polygala tenuifolia* extract, the *Angelica dahurica* extract and the *Elsholtzia splendens* extract may be mixed at a weight ratio of 0.5-1.5:1.5-2.5:0.05-0.15 (w/w).

In an unlimited example of the present invention, the *Polygala tenuifolia* extract, the *Angelica dahurica* extract and the *Elsholtzia splendens* extract may be mixed at a weight ratio of 0.5:1.5:1, 1.5:0.5:1, 0.1:1.95:0.95, 0.5:0.5:2, 0.95:1.95:0.1 or 1.45:0.1:1.45 (w/w).

The cosmetic composition of the present invention may further include one or more cosmetically acceptable carriers that are blended into general skin cosmetics. Also, as common ingredients, for example, but not limited to, oils, water, surfactants, moisturizers, lower alcohols, thickeners, chelating agents, pigments, preservatives, fragrances, etc. may be blended, as appropriate.

When the cosmetic formulation of the present invention is an ointment, a paste, a cream, or a gel, carrier ingredients such as animal oils, vegetable oils, waxes, paraffins, starches, tragacanth, cellulose derivatives, polyethylene glycol, silicone, bentonite, silica, talc, zinc oxide, etc. may be used, but they are not limited thereto. These may be used alone or in combination of two or more thereof.

When the formulation of the present invention is a solution or an emulsion, carrier ingredients such as a solvent, a solubilizing agent, an emulsifying agent, etc., for example, water, ethanol, isopropanol, ethyl carbonate, ethyl acetate, benzyl alcohol, benzyl benzoate, propylene glycol, 1,3-butyl glycol oil, etc., particularly, cottonseed oils, peanut oils, corn germ oils, olive oils, castor oils and sesame oils, glycerol aliphatic esters, polyethylene glycol or fatty acid esters of sorbitan may be used, but they are not limited thereto. These may be used alone or in combination of two or more thereof.

When the formulation of the present invention is a suspension, carrier ingredients such as liquid diluents such as water, ethanol or propylene glycol, suspending agents such as ethoxylated isostearyl alcohol, polyoxyethylene sorbitol ester and polyoxyethylene sorbitan ester, microcrystalline cellulose, aluminum metahydroxide, bentonite, agar, tragacanth, etc. may be used, but they are not limited thereto. These may be used alone or in combination of two or more thereof.

When the formulation of the present invention is a soap, carrier ingredients such as alkali metal salts of fatty acids, hemiester salts of fatty acids, fatty acid protein hydrolyzates, isethionates, lanolin derivatives, fatty alcohols, vegetable oils, glycerol, sugars, etc. may be used, but they are not limited thereto. These may be used alone or in combination of two or more thereof.

When the formulation of the present invention is a powder or a spray, carrier ingredients such as lactose, talc, silica, aluminum hydroxide, calcium silicate, polyamide powders, or mixtures thereof may be used. Particularly, in the case of a spray, it may further include propellants such as chloro fluorohydrocarbon, propane/butane or dimethyl ether.

The cosmetic composition according to the present invention inhibits DPPH (1-1-diphenyl-2-picryl-hydrazyl) and ABTS (2,2'-azinobis-(3-ethylbenzothiazoline-6-sulfonic acid) activities and suppresses NO (nitric oxide) production, and thus has excellent anti-inflammatory effects and antioxidant effects on the skin. Specifically, the composition according to the present invention was confirmed to have excellent antioxidant and anti-inflammatory effects at all mixing ratios. Especially, it was confirmed to have particularly excellent effects at a specific mixing ratio (see FIG. 1, FIG. 2, and FIG. 4 of the present invention).

It was confirmed that the cosmetic composition according to the present invention not only has antioxidant and anti-inflammatory effects, but also has an excellent moisturizing effect by promoting the production of hyaluronic acid in keratinocytes and has excellent antibacterial activity against specific strains (see FIG. 6 and Table 2). In particular, it was confirmed that the cosmetic composition according to the present invention has excellent antibacterial activity against the strains of a specific genus (*Staphylococcus*).

Another aspect of the present invention is a pharmaceutical composition for treating, preventing, alleviating or inhibiting inflammatory skin diseases comprising a *Polygala tenuifolia* extract, an *Angelica dahurica* extract and an *Elsholtzia splendens* extract as active ingredients.

In the present invention, the pharmaceutical composition includes extracts of *Polygala tenuifolia, Angelica dahurica* and *Elsholtzia splendens* in the same manner as the cosmetic composition according to the present invention as described above, and the descriptions of overlapping contents between the two inventions will be omitted to avoid excessive complexity of the present specification.

As used herein, the term "comprising as active ingredients" means comprising an amount sufficient to achieve the efficacy or activity of the extract. The upper quantitative limit of the extract included in the composition of the present invention can be selected and implemented within an appropriate range by a person skilled in the art. According to an embodiment of the present invention, the composition of the present invention may be implemented as a pharmaceutical composition, cosmetic composition, or food composition comprising extracts of *Polygala tenuifolia, Angelica dahurica* and *Elsholtzia splendens* as active ingredients.

The content of the extracts as active ingredients in the composition according to the present invention may be appropriately adjusted depending on the form used and its purpose, patient's condition, type and severity of symptoms, etc. It may be for example, but not limited to, 0.001 to 99.9% by weight, or 0.1 to 99.9% by weight, based on the weight of solids.

The daily dose of the composition according to the present invention can be appropriately adjusted depending on the form used and its purpose, patient's condition, type and severity of symptoms, etc. The daily dose of the active ingredients may be 1 to 1000 μg/ml, for example, 0.001 to 10000 mg/kg, but is not limited thereto.

The composition according to the present invention may be administered to mammals, including humans, via various routes. Administration may be conducted in any typical mode. For example, it may be administered orally, dermally, intravenously, intramuscularly, subcutaneously, etc. For example, it may be administered orally.

The composition according to the present invention may be formulated into oral dosage forms such as powders, granules, tablets, capsules, ointments, suspensions, emulsions, syrups, aerosols, etc., or into parenteral dosage forms in the form of transdermal preparations, suppositories, and sterile injectable solutions, according to conventional methods.

In an embodiment of the present invention, the composition may further contain pharmaceutically suitable and physiologically acceptable adjuvants such as carriers, excipients, diluents, etc., in addition to the mixed extracts.

Examples of the carriers, excipients and diluents that may be included in the composition of the present invention include, but not limited to, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and mineral oils.

When formulated, diluents or excipients such as fillers, extenders, binders, wetting agents, disintegrants, surfactants, etc. commonly used in the art may be used. Examples of solid formulations for oral administration may include tablets, pills, powders, granules, capsules, etc., and these solid formulations may be prepared by mixing the extracts with at least one excipient, such as starch, calcium carbonate, sucrose, lactose, gelatin, etc. In addition to simple excipients, lubricants, such as but not limited to, magnesium stearate and talc can also be used.

Examples of formulations for oral use include suspensions, oral liquids, emulsions, syrups, ointments, etc. In addition to commonly used simple diluents such as water and liquid paraffin, various excipients such as, but not limited to, wetting agents, sweeteners, fragrances, preservatives, etc. may be included.

Examples of formulations for parenteral administration include sterilized aqueous solutions, non-aqueous solvents, suspensions, emulsions, freeze-dried preparations, suppositories, transdermal preparations, etc. Examples of the non-aqueous solvents and suspensions may include, but are not limited to, propylene glycol, polyethylene glycol, vegetable oils such as olive oils, and injectable esters such as ethyl oleate.

Examples of suppository bases may include, but not limited to, Witepsol, Macrogol, Tween 61, cacao butter, laurin butter, glycerogenatin, etc.

Yet another aspect of the present invention is a food composition for alleviating, inhibiting or improving inflammatory skin diseases comprising a *Polygala tenuifolia* extract, an *Angelica dahurica* extract and an *Elsholtzia splendens* extract as active ingredients.

In an embodiment of the present invention, the food composition may be, but not limited to, various foods, beverages, food additives, etc.

The food composition according to the present invention may include ingredients commonly added during food production, for example, but not limited to, proteins, carbohydrates, fats, nutrients, seasonings and flavoring agents.

Examples of carbohydrates that may be included in the food composition according to the present invention include, but not limited to, monosaccharides such as glucose, fructose, etc., disaccharides such as maltose, sucrose, oligosaccharides, etc., polysaccharides such as dextrin, cyclodextrin, etc. and sugar alcohols such as xylitol, sorbitol, erythritol, etc.

Examples of flavoring agents that may be included in the food composition according to the present invention may include, but not limited to, natural flavoring agents such as thaumatin, *stevia* extract, etc. and synthetic flavoring agents such as saccharin, aspartame, etc.

Yet another aspect of the present invention is a method for improving skin, comprising the step of administering to a subject a composition comprising a *Polygala tenuifolia* extract, an *Angelica dahurica* extract and an *Elsholtzia splendens* extract.

Yet another aspect of the present invention is a method for treating inflammatory skin diseases, comprising the step of administering to a subject a composition comprising a *Polygala tenuifolia* extract, an *Angelica dahurica* extract and an *Elsholtzia splendens* extract.

As used herein, the term "administration" refers to providing a given substance to a subject by any suitable method. The route of administration of the composition for alleviating, inhibiting, treating or preventing allergic diseases of the present invention may be oral or parenteral administration through all general routes as long as it can reach the target tissue. Additionally, the composition of the present invention may be administered using any device capable of delivering the active ingredients to target cells.

As used herein, the term "subject" includes humans, monkeys, cattle, horses, sheep, pigs, chickens, turkeys, quail, cats, dogs, mice, rats, rabbits or guinea pigs. It refers to, for example, but not limited to, mammals, specifically humans.

In an embodiment of the present invention, the extract composition of the present invention may generally be administered in combination with a pharmaceutical carrier selected in consideration of the mode of administration and standard pharmaceutical practice, although it may be administered alone.

For example, the herbal extract-containing composition of the present invention may be administered orally, intraorally, or sublingually in the form of tablets containing starch or lactose, or in the form of capsules containing the composition alone or in mixture with excipients, or in the form of elixirs or suspensions containing chemicals that add flavor or color. These liquid formulations may be formulated with pharmaceutically acceptable additives such as suspending agents (e.g. methylcellulose, semi-synthetic glycerides such as Witepsol or a mixture of apricot kernel oil and PEG-6 ester or glyceride mixtures such as a mixture of PEG-8 and caprylic/capric glycerides).

The dose of the herbal extract-containing composition of the present invention may vary depending on the patient's age, weight, gender, form of administration, health condition, and degree of disease, and may be administered once a day or several times a day at regular time intervals according to the judgment of a doctor or pharmacist.

For example, the daily dose of the active ingredients may be 1 to 1000 μg/ml, but this is an example of an average case, and the dose may be higher or lower depending on individual differences.

Advantageous Effects of Invention

The present invention relates to a composition for improving skin comprising extracts of *Polygala tenuifolia*, *Angelica dahurica* and *Elsholtzia splendens*. The composition is excellent in effects of improving skin inflammation, antioxidant effects, antibacterial effects on skin, and skin moisturizing effects, and thus can be used as a cosmetic for improving skin, and further, as a pharmaceutical composition for treating inflammatory skin diseases.

DESCRIPTION OF EMBODIMENTS

Examples

Figure 1:
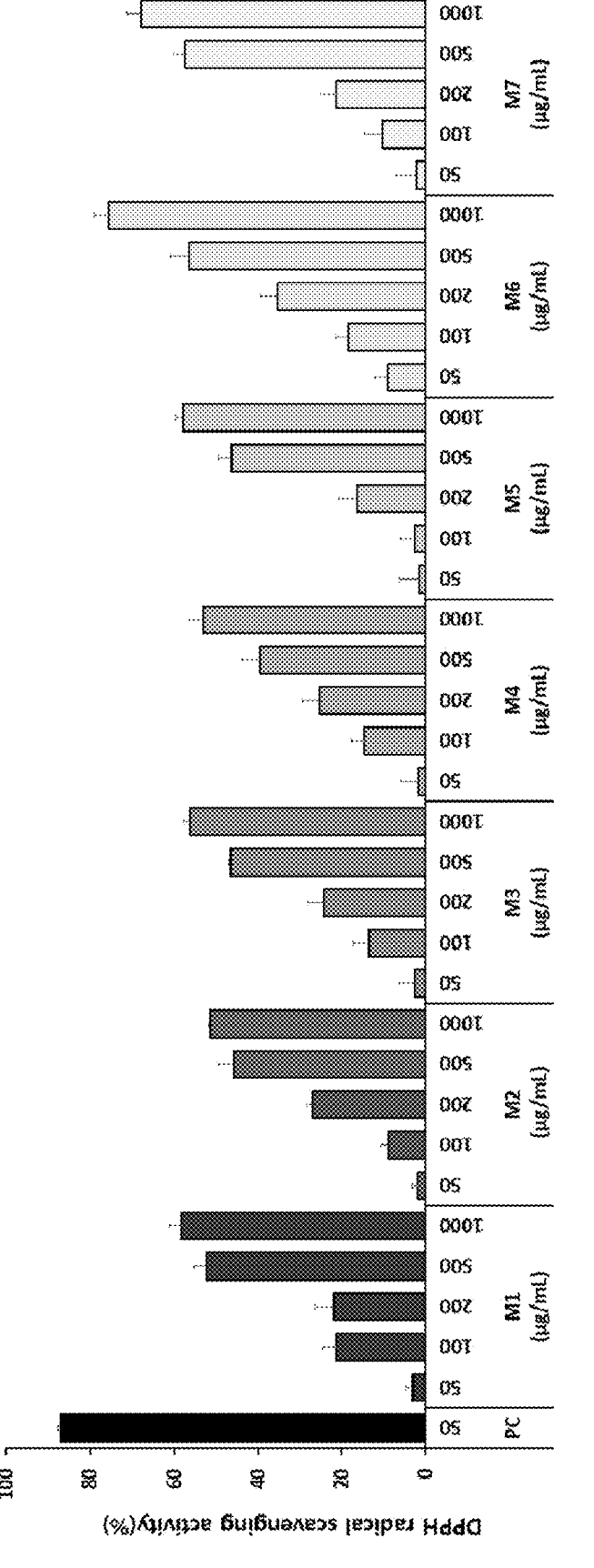
FIG. 1 is a graph showing the results of measuring the DPPH radical scavenging activity of the samples of mixed extracts of *Polygala tenuifolia*, *Angelica dahurica* and *Elsholtzia splendens* according to an example of the present invention.

Hereinafter, the present invention will be described in more detail through the following examples. However, these examples are only for illustrating the present invention, and the scope of the present invention is not limited by these examples.

Example 1: Materials and Methods 1-1. Reagents and Equipment

The reagents used were ascorbic acid (AA, Sigma-Aldrich, USA), 1,1-diphenyl-2-picryl-hydrazyl (DPPH, Sigma, USA), 2,2'-azinobis-(3-ethylbenzothiazoline-6-sulfonic acid) (ABTS, Sigma, USA), Dulbecco's Modified Eagles Medium (DMEM, Welgene, Korea), fetal bovine serum (FBS, Gibco, USA), FBS (Samchun, Korea), penicillin/streptomycin (Lonza, Switzerland), water-soluble tetrazolium salt (WST)-8 (Biomax, Korea), lipopolysaccharide (LPS, SigmaAldrich, USA), Griess reagent system (Promega, USA), hyaluronic acid (HA), enzyme linked immunosorbent assay (ELISA) kit (Minneapolis, USA).

The experimental equipment used was a grinder (Hanil, Korea), a rotary vacuum evaporator (BUCHI, Germany), an incubator (Thermo, USA), a microplate reader (BioTek, USA), and a pipette (Eppendorf, Germany).

1-2. Materials

The *Polygala tenuifolia, Angelica dahurica* and *Elsholtzia splendens* used for extraction were purchased from Jecheon Oriental Herbal Medicine (Jecheon, Korea) after going through a washing and drying process, and were used after grinding.

1-3. Sample Extraction and Mixing 400 mL of 70% ethanol was added to 100 g of each of ground *Polygala tenuifolia, Angelica dahurica* and *Elsholtzia splendens* and extraction was performed at room temperature for 48 hours. The extract was filtered through filter paper and concentrated at 45° C. using a rotary vacuum evaporator, and the concentrated powder was stored at −50° C. for use in the experiment.

With regard to the mixing ratio of *Polygala tenuifolia, Angelica dahurica* and *Elsholtzia splendens*, seven mixing ratios as shown in Table 1 were used for the *Polygala tenuifolia* extract, the *Angelica dahurica* extract and the *Elsholtzia splendens* extract. Mixtures were prepared according to the ratios.

TABLE 1

| Sample | Polygala teuifolia | Angelicae dahurica | Elsholtzia splendens |
|---|---|---|---|
| M1 | 1 | 1 | 1 |
| M2 | 0.5 | 1.5 | 1 |
| M3 | 1.5 | 0.5 | 1 |
| M4 | 0.1 | 1.95 | 0.95 |
| M5 | 0.5 | 0.5 | 2 |
| M6 | 0.95 | 1.95 | 0.1 |
| M7 | 1.45 | 0.1 | 1.45 |

1-4. Evaluation of Antioxidant Efficacy

DPPH Radical Scavenging Assay

Antioxidant efficacy was measured by DPPH radical scavenging activity based on the Blois' method. This assay is one of the generation methods. DPPH is purple in the radical state, and when reduced by receiving electrons, it changes its color to yellow (DPPH-H). 100 μL of 0.2 mM DPPH solution and 80 μL of samples of each concentration were mixed in a 96-well plate, reacted for 30 minutes at room temperature in the dark, and then absorbance was measured at 517 nm to calculate radical scavenging activity according to Equation 1 below. Ascorbic acid, an antioxidant, was used as a positive control, and a DPPH solution which was not treated with a sample was used as a negative control.

$$DPPH \text{ radical scavenging assay } (\%) = \qquad [\text{Equation 1}]$$
$$(1 - \text{ansorbance of the group with sample added/}$$
$$\text{absorbance of the group without sample}) \times 100$$

ABTS Radical Scavenging Assay

Antioxidant activity was measured using 2,2-azino-biazoline-6-sulphonic acid (ABTS) radical with reference to the Van den Berg method. This method uses the principle that ABTS+ radical, which has a blue-green color, is made to be transparent by antioxidants. 7 mM ABTS and 2.4 mM potassium persulfate were mixed and left at room temperature in the dark for 24 hours to form ABTS. Absorbance was measured at 734 nm, and the material was used for the experiment after adjusting the absorbance to 0.7±0.1.

100 μL of ABTS working solution and 100 μL of samples of each concentration were mixed and reacted in the dark for 10 minutes. Then, the absorbance was measured at 732 nm and the radical scavenging activity was calculated as shown in Equation 2 below. Ascorbic acid, an antioxidant, was used as a positive control, and an ABTS solution which was not treated with a sample was used as a negative control.

$$ABTS \text{ radical scavenging assay } (\%) = \qquad [\text{Equation 2}]$$
$$(1 - \text{absorbance of the group with sample added/}$$
$$\text{absorbance of the group without sample}) \times 100$$

1-5. Cell Culture

Raw 264.7 cells were provided by the Korea Cell Line Bank (KCLB; Seoul, Korea), and human keratinocyte cell line (HaCaT) cells were provided by Amore Pacific (Korea). For cell culture, DMEM containing 10% FBS and 1% penicillin/streptomycin was used, and the cells were cultured in an incubator at 5% carbon dioxide and 37° C.

1-6. Cell Viability Test

Cells were dispensed into a 96-well plate at $1\times10^4$ cells/well, and then cultured in an incubator for 24 hours to allow complete attachment, and thereafter treated with samples for 48 hours. WST-8 was added at a 10% concentration and reacted for 2 hours, and then absorbance was measured at 450 nm with a microplate reader.

1-7. Measurement of Nitric Oxide (NO) Inhibitory Activity

Raw 264.7 cells were dispensed into a 96-well plate at $1\times10^4$ cells/well, and then cultured in an incubator for 24 hours to allow complete attachment, and thereafter treated with samples for 48 hours. The stimulating source was LPS at a concentration of 10 ng/mL. The culture supernatant was taken and the amount of NO produced was quantified using the Griess reagent system according to the manufacturer's guidelines.

1-8. Measurement of Hyaluronic Acid (HA)

HaCaT cells were dispensed into a 96-well plate at $1\times10^4$ cells/well, and then cultured in an incubator for 24 hours to allow complete attachment, and thereafter treated with samples for 48 hours. Retinoic acid was used as a positive control. The supernatant of the cultured cells was taken, and the amount of hyaluronic acid produced was measured by the ELISA assay according to the manufacturer's guidelines.

1-9. Antibacterial Activity

The antibacterial effect was measured against *Staphylococcus aureus* (*S. aureus*). The paper disc method was used to measure the antibacterial activity of the samples. Each strain cultured on a solid plate medium was taken by a platinum loop, then inoculated into a 4 mL liquid medium, and cultured for 20 hours to activate it. Then, 500 μL of the strain was inoculated into 3 mL of liquid medium and cultured for 4 hours. The strain was inoculated onto a solid plate medium so that the number of bacteria was $1\times10^6$-$5\times10^6$/mL, and then spread evenly using a spreader. Each sample was prepared according to the concentrations, and 50 μL of the sample was absorbed into a paper disc (Toyo, Japan) with a diameter of 8 mm. The paper disc was placed on a solid plate medium inoculated with the strain and cultured at 37° C. for 20 hours. Then, the diameter of the clear zone around the disc was measured.

1-10. Statistical Processing

All experiments were repeated three times, and the results were expressed as mean±standard deviation. Results were considered statistically significant when the p value was less than 0.05 in independent sample t-test and one-way ANOVA using SPSS 18.0 program.

Example 2: DPPH and ABTS Radical Scavenging Activities

Figure 2:
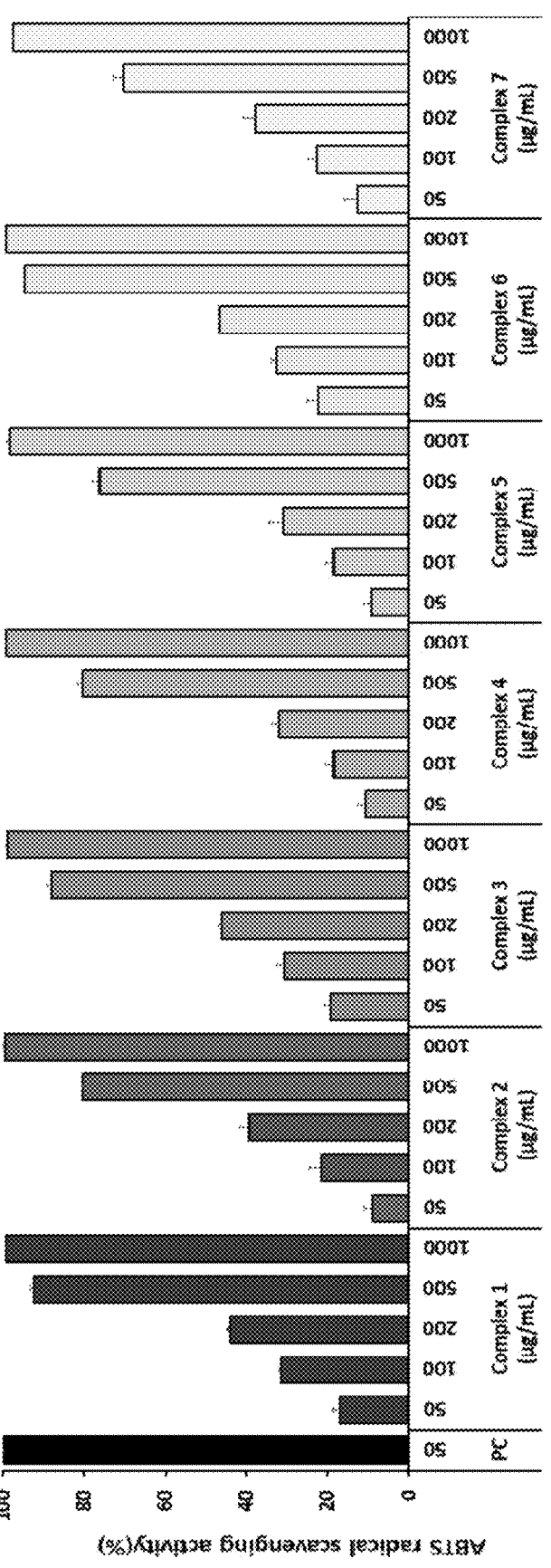
FIG. 2 is a graph showing the results of measuring the ABTS radical scavenging activity of the samples of mixed extracts of *Polygala tenuifolia*, *Angelica dahurica* and *Elsholtzia splendens* according to an example of the present invention.

Radicals are unstable and thus easily react with cellular components, causing non-selective and irreversible damage. The DPPH radical, which displays a purple color, is a relatively stable compound and is used to test radical activity through reaction with antioxidants. The DPPH and ABTS radical scavenging activities of the extracts are shown in FIG. 1 and FIG. 2.

As for DPPH radical scavenging activity, M6, which has a high mixing ratio of *Polygala tenuifolia* and *Elsholtzia splendens*, showed the highest activity of 9.05±2.78-75.37±3.79% at a concentration of 50-1,000 μg/mL. Ascorbic acid, which is used as a positive control (PC), showed antioxidant activity of 87.21±0.56% at a concentration of 50 μg/mL. DPPH radical scavenging activity of other mixed extracts at a concentration of 50-1,000 μg/mL was high in the order of M7 (2.10±4.91-67.83±3.44%), M1 (2.96±1.71-58.21±2.81%), M5 (1.34±4.48-57.74±1.87%), M3 (2.48±3.58-56.21±1.48%), M4 (0.47±4.12-52.95±3.29%) and M2 (1.73±1.33-51.35±0.36%). The activity increased in a concentration-dependent manner in all samples.

ABTS radical scavenging activity increased with increasing concentration in all mixed extracts. In particular, at a concentration of 50-1,000 μg/mL, M6 showed the highest activity of 22.32±2.62-99.19±0.20%, showing a similar trend to its DPPH radical scavenging activity. ABTS radical scavenging activity increased in a concentration-dependent manner in all mixed extracts, and ascorbic acid, used as a positive control (PC), showed antioxidant activity of 99.68±0.21% at a concentration of 50 μg/mL. At a concentration of 500 μg/mL, M6 showed a significantly high activity of 94.61±0.13%, followed by M1 (92.30±1.04%), M3 (87.87±1.32%), M2 (80.42±0.11%), M4 (80.31±1.22%), M5 (76.27±1.44%), and M7 (70.59±2.06%).

Example 3: Raw 264.7 Cell Viability

Figure 3:
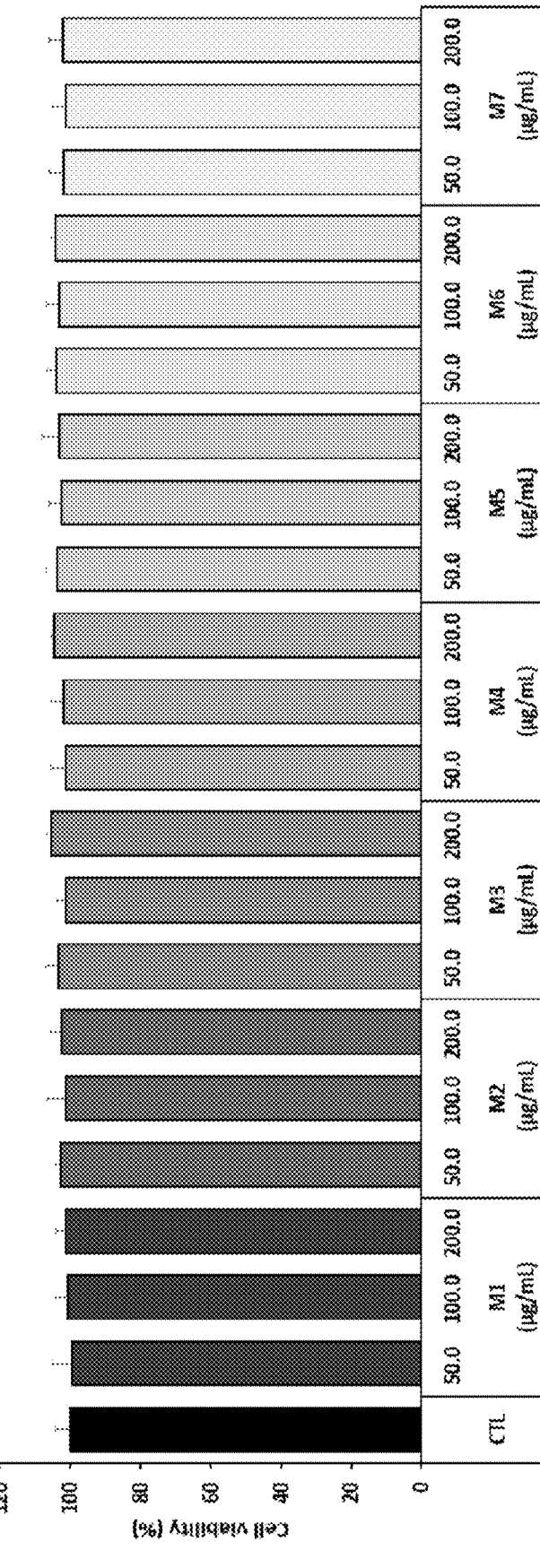
FIG. 3 is a graph showing the results of measuring the cell viability after treating Raw 264.7 cells with the samples of mixed extracts of *Polygala tenuifolia*, *Angelica dahurica* and *Elsholtzia splendens* according to an example of the present invention.

WST-8 assay was performed to determine the effect of mixed extracts of *Polygala tenuifolia, Angelica dahurica* and *Elsholtzia splendens* on the viability of Raw 264.7 cells, and the results are shown in FIG. 3. The concentrations of all mixed extracts were set to 50, 100, and 200 μg/mL. Since they did not show toxicity at any concentrations, the maximum concentration was set to 200 μg/mL, and NO production was measured.

Example 4: NO Production in Raw 264.7 Cells

Figure 4:
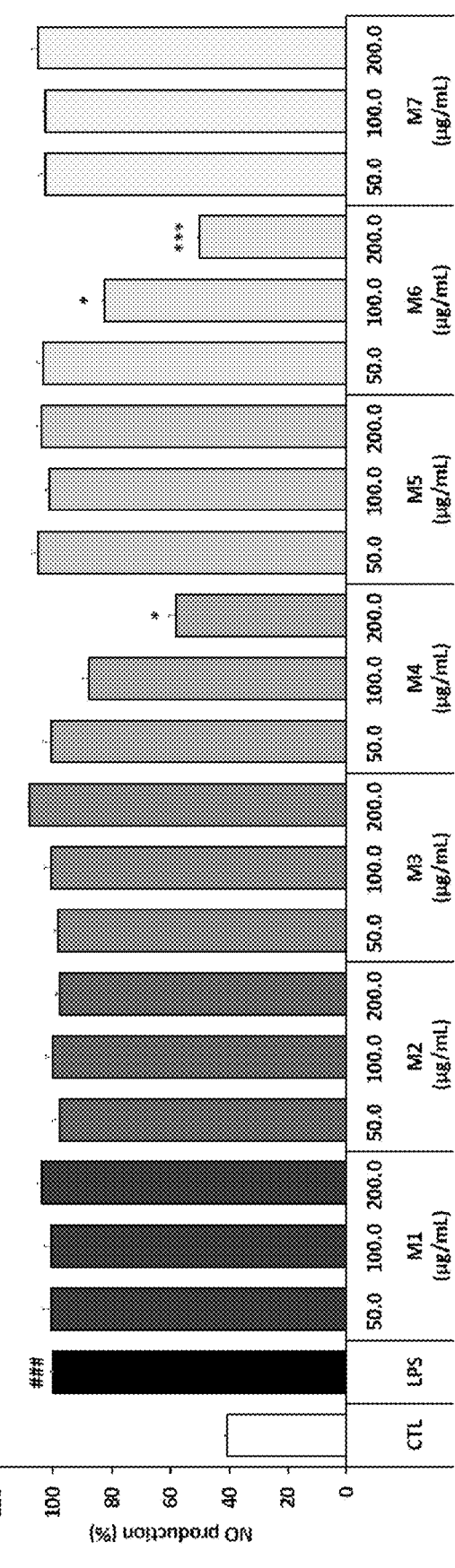
FIG. 4 is a graph showing the results of measuring the NO production in Raw 264.7 cells after treating the Raw 264.7 cells with the samples of mixed extracts of *Polygala tenuifolia*, *Angelica dahurica* and *Elsholtzia splendens* according to an example of the present invention.

To compare the effects of mixed extracts at various ratios on NO production, an inflammatory response was induced in Raw 264.7 cells by LPS, and then the cells were treated with the mixed extracts at concentrations of 50, 100, and 200 μg/mL. Thereafter, the Griess assay was performed. As shown in FIGS. 4, M4 and M6 showed high NO production inhibitory activity in a concentration-dependent manner, and in particular, at a concentration of 200 μg/mL, M6 showed about 50% production compared to the LPS-treated group and displayed statistically significant NO production inhibitory activity.

Example 5: HaCaT Cell Viability

Figure 5:
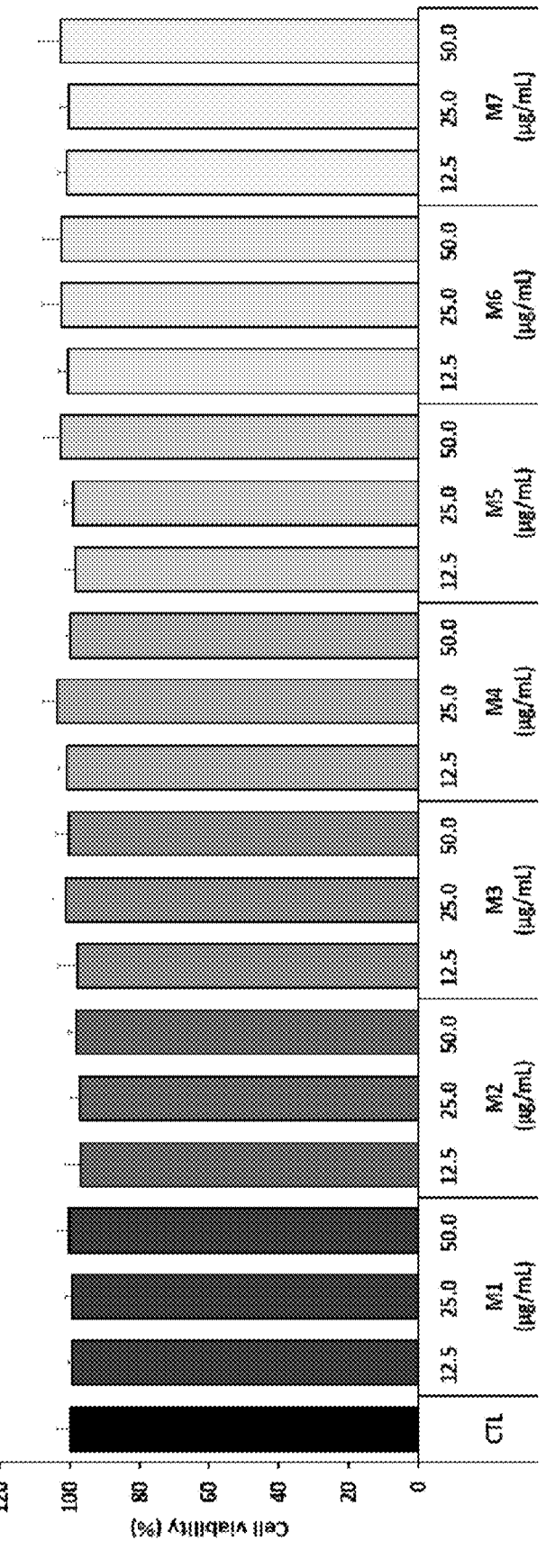
FIG. 5 is a graph showing the results of measuring the cell viability of the cells of the human keratinocyte cell line (HaCaT) after treating the cells with the samples of mixed extracts of *Polygala tenuifolia*, *Angelica dahurica* and *Elsholtzia splendens* according to an example of the present invention.

WST-8 assay was performed to determine the effect of mixed extracts of *Polygala tenuifolia, Angelica dahurica* and *Elsholtzia splendens* on the viability of HaCaT cells. The concentrations were set to 50, 100, and 200 μg/mL. As shown in FIG. 5, the mixed extracts did not show toxicity at a concentration range of 12.5-50.0 μg/mL, and thus the maximum concentration was set to 50.0 μg/mL, and hyaluronic acid production was measured.

Example 6: Hyaluronic Acid Production by HaCaT Cells

Figure 6:
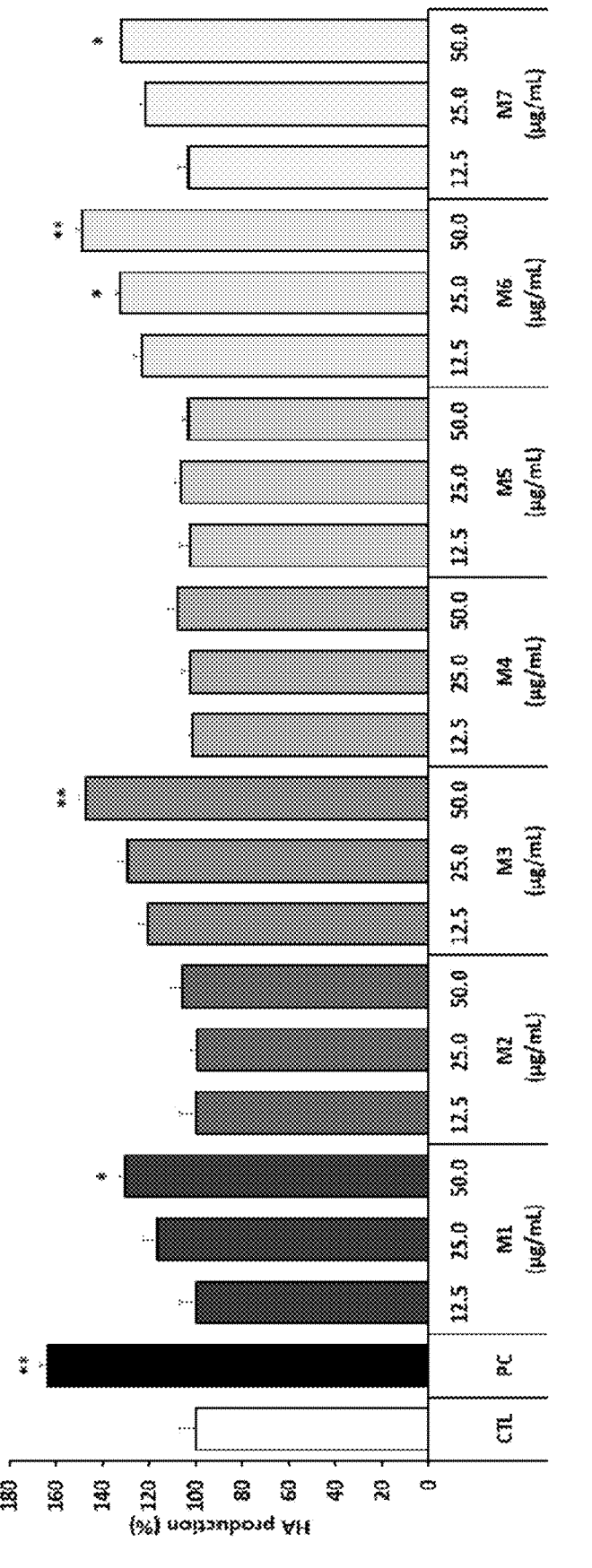
FIG. 6 is a graph showing the results of measuring the hyaluronic acid production in HaCaT cells after treating the cells with the samples of mixed extracts of *Polygala tenuifolia*, *Angelica dahurica* and *Elsholtzia splendens* according to an example of the present invention.

In order to determine the effect of the mixed extracts at various ratios on moisturizing effect, HaCaT cells were treated with 12.5, 25.0, and 50.0 μg/mL of each mixed extract. The culture medium recovered after culturing the cells for 48 hours was analyzed for hyaluronic acid production using an ELISA kit. The results are shown in FIG. 6. The content of HA contained in skin tissues amounts to 50% of the total HA in the human body, and when HA in the skin decreases due to various factors, it is directly linked to skin aging, including loss of skin moisture. HA is widely used as a general indicator in the search for skin moisturizing materials in various in vitro models. After treating HaCaT cells with the mixed extracts at a concentration range that did not show cytotoxicity, HA production was evaluated. The results showed that all mixed extracts displayed concentration-dependent HA production enhancing activity in the concentration range of 12.5-50.0 μg/mL, and at a concentration of 50 μg/mL, M3 and M6 displayed statistically significantly increased (1.47-fold, 1.49-fold) HA production activity compared to the control.

Example 7: Antibacterial Test Results

Disc diffusion test is performed by placing a disc into which a sample was absorbed on an agar plate medium inoculated with bacteria and culturing them, and then measuring the diameter of the inhibition zone (clear zone) of the sample that diffused around the disc as much as it inhibited the growth of the bacteria.

Table 2 below shows the experimental results for *Staphylococcus aureus* strain. Methyl paraben, used as a positive control, showed 8.5 mm at 4 mg/mL, and M4 and M6 showed 8.75±0.25 and 9.75±0.25 mm at 8 mg/mL, showing the effect of inhibiting the growth of *Staphylococcus aureus* strain.

TABLE 2

| Sample | Concentration (mg/mL) | Clear zone (mm) |
|---|---|---|
| Methyl paraben | 4 | 8.5 |
| M1 | 8 | — |
| M2 | 8 | — |
| M3 | 8 | — |
| M4 | 8 | 8.75 ± 0.25 |
| M5 | 8 | — |
| M6 | 8 | 9.75 ± 0.25 |
| M7 | 8 | — |

The invention claimed is:

1. A method for improving skin inflammation, skin anti-oxidation, antibacterial effects on skin, moisturizing effects on skin, and nitric oxide production inhibitory effects on skin, the method comprising:

administering to a subject, a cosmetic composition comprising a *Polygala tenuifolia* extract, an *Angelica dahurica* extract and an *Elsholtzia splendens* extract as active ingredients, wherein the *Polygala tenuifolia* extract, the *Angelica dahurica* extract, and the *Elsholtzia splendens* extract are mixed at a weight ratio of 0.1-0.95:1.95:0.1-0.95 (w/w).

2. The method of claim 1, wherein the *Polygala tenuifolia* extract, the *Angelica dahurica* extract and the *Elsholtzia splendens* extract are extracted with at least one solvent selected from water, alcohols having 1 to 4 carbon atoms, or mixed solvents thereof.

3. The method of claim 1, wherein the cosmetic composition inhibits DPPH (1-1-diphenyl-2-picryl-hydrazyl) and ABTS (2,2'-azinobis-(3-ethylbenzothiazoline-6-sulfonic acid) activities.

4. The method of claim 1, wherein the cosmetic composition inhibits NO (nitric oxide) production.

5. The method of claim 1, wherein the *Polygala tenuifolia* extract, the *Angelica dahurica* extract and the *Elsholtzia splendens* extract are mixed at a weight ratio of 0.05-3:0.05-3:0.05-3 (w/w).

6. The method of claim 1, wherein the cosmetic composition is at least one formulation selected from a group consisting of serums, tonics, essences, pastes, mask packs, patches, gels, creams, lotions, nourishing lotions, nourishing creams, moisturizing creams, massage creams, powders, soaps, cleansers, oils, foundations, makeup bases, waxes, and sprays.

7. The method of claim 1, wherein the skin inflammation is any one or more selected from a group consisting of dermatitis, allergic dermatitis, irritant dermatitis, seborrheic dermatitis, atopic dermatitis, sensitive skin diseases, pruritus, eczematous skin diseases, dry eczema, erythema, urticaria, psoriasis, drug rash, and acne.

8. A method for improving treating inflammatory skin disease, the method comprising:

administering to a subject, a composition comprising a *Polygala tenuifolia* extract, an *Angelica dahurica* extract and an *Elsholtzia splendens* extract as active ingredients, wherein the *Polygala tenuifolia* extract, the *Angelica dahurica* extract and the *Elsholtzia splendens* extract are mixed at a weight ratio of 0.1:1.95:0.95 or 0.95:1.95:0.1 (w/w).

9. The method of claim 8, wherein the inflammatory skin disease is at least one selected from a group consisting of dermatitis, allergic dermatitis, irritant dermatitis, seborrheic dermatitis, atopic dermatitis, sensitive skin diseases, pruritus, eczematous skin diseases, dry eczema, erythema, urticaria, psoriasis, drug rash, and acne.

* * * * *